United States Patent
Cazaux et al.

(10) Patent No.: US 9,260,358 B2
(45) Date of Patent: Feb. 16, 2016

(54) PROCESS FOR OLIGOMERIZATION OF OLEFINS THAT USES A CATALYTIC COMPOSITION THAT COMPRISES AN ORGANOMETALLIC COMPLEX THAT CONTAINS A PHENOXY LIGAND THAT IS FUNCTIONALIZED BY A HETEROATOM

(75) Inventors: Jean-Benoit Cazaux, Lyons (FR); Lionel Magna, Lyons (FR); Lucien Saussine, Charly (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 1701 days.

(21) Appl. No.: 12/599,882

(22) PCT Filed: Apr. 14, 2008

(86) PCT No.: PCT/FR2008/000526
§ 371 (c)(1),
(2), (4) Date: May 20, 2011

(87) PCT Pub. No.: WO2008/142295
PCT Pub. Date: Nov. 27, 2008

(65) Prior Publication Data
US 2011/0213190 A1    Sep. 1, 2011

(30) Foreign Application Priority Data

May 14, 2007   (FR) ..................................... 07 03505

(51) Int. Cl.
| | | |
|---|---|---|
| *C07C 2/30* | (2006.01) | |
| *C07C 2/36* | (2006.01) | |
| *B01J 31/02* | (2006.01) | |
| *B01J 31/22* | (2006.01) | |
| *C07C 2/32* | (2006.01) | |

(52) U.S. Cl.
CPC .............. *C07C 2/36* (2013.01); *B01J 31/0214* (2013.01); *B01J 31/2217* (2013.01); *C07C 2/32* (2013.01); *B01J 2231/20* (2013.01); *B01J 2523/47* (2013.01); *B01J 2523/48* (2013.01); *B01J 2523/49* (2013.01); *B01J 2531/0238* (2013.01); *C07C 2531/14* (2013.01); *C07C 2531/22* (2013.01); *C07C 2531/24* (2013.01)

(58) Field of Classification Search
CPC .......................... B01J 31/0214; B01J 31/2217
USPC ......... 585/510, 511, 512, 513, 520, 521, 522, 585/523, 524, 526, 527
See application file for complete search history.

(56) References Cited

U.S. PATENT DOCUMENTS

| | | | | |
|---|---|---|---|---|
| 6,350,831 | B1 * | 2/2002 | Takemori et al. ............. | 526/160 |
| 6,531,555 | B2 * | 3/2003 | Whiteker ....................... | 526/161 |
| 6,593,266 | B1 * | 7/2003 | Matsui et al. ................. | 502/103 |
| 6,730,626 | B2 * | 5/2004 | Kashiwamura et al. ...... | 502/121 |
| 7,109,284 | B2 * | 9/2006 | Ishii et al. ..................... | 526/352 |

FOREIGN PATENT DOCUMENTS

| | | |
|---|---|---|
| EP | 0722922 A1 | 7/1996 |
| JP | 58201729 A | 11/1983 |
| JP | 58201729 W | 11/1983 |
| WO | PCTFR0800526 R | 11/2008 |

OTHER PUBLICATIONS

Deckers, P. J. W.; Hessen, B.; Teuben, J. H. "Catalytic Trimerization of Ethene with Highly Active Cyclopentadienyl-Arene Titanium Catalysts" Organometallics (2002), 21, 5122-5135.*
Wu, T.; Qian, Y.; Huang, J. "Catalytic trimerization of ethylene by half-sandwich titanium complexes bearing a pendant ethereal group" Journal of Molecular Catalysis A: Chemical (2004), 214, 227-229.*
Uglea, C. V. "Oligomer Technology and Applications" Marcel Dekker, Inc.: New York, 1998, p. 9.*
Jamanek, D. et al. "Effect of phenoxy ligands on catalytic properties of titanium half-sandwich complexe/MAO systems." (Journal of Molecular Catalysis A: Chemical), May 11, 2006, 192-196, vol. 254.

* cited by examiner

*Primary Examiner* — In Suk Bullock
*Assistant Examiner* — Aaron Pierpont
(74) *Attorney, Agent, or Firm* — Millen White Zelano and Branigan, PC; Csaba Henter; Anthony Zelano

(57) ABSTRACT

The invention describes a process for oligomerization of the olefins into compounds or into a mixture of compounds of general formula CpH2p with 4≤p≤80 that implements a catalytic composition that comprises at least one organometallic complex of an element of group IV that is selected from among titanium, zirconium, or hafnium, whereby said organometallic complex contains at least one aryloxy-type (or phenyloxy-type) ligand that is functionalized by a heteroatom that is selected from among nitrogen, oxygen, phosphorus or sulfur or by an aromatic group.

24 Claims, No Drawings

PROCESS FOR OLIGOMERIZATION OF OLEFINS THAT USES A CATALYTIC COMPOSITION THAT COMPRISES AN ORGANOMETALLIC COMPLEX THAT CONTAINS A PHENOXY LIGAND THAT IS FUNCTIONALIZED BY A HETEROATOM

This invention relates to the oligomerization of olefins, in particular ethylene. The oligomerization is defined as the transformation of a monomeric unit into a compound or a mixture of compounds of general formula $C_pH_{2p}$ such as $4 \leq p \leq 80$.

One object of the invention is to provide a process for oligomerization of olefins, preferably of ethylene, propylene and butene, and in a preferred manner of ethylene, using a particular catalytic composition.

It is well known that the monoolefins-α, such as ethylene, propylene or butene-1, can be oligomerized with catalytic systems based on transition metals, such as nickel, chromium, titanium, zirconium or other metals, in the presence of a co-catalyst such as a hydrocarbylaluminum compound, a hydrocarbylaluminum halide, or an aluminoxane.

Several types of ligands have been described for stabilizing the catalytic radical and orienting the selectivity of the oligomerization reaction.

The U.S. Pat. No. 3,660,519 claims a catalytic composition for oligomerizing the ethylene that limits the proportion of oligomers of greater than C22. This catalytic composition comprises: (a) a titanium compound of formula $[Ti(OR)_n(Cl)_{4-n}]$ (with n=1 to 4, and whereby R is an alkyl group); (b) an electron-donor organic compound that contains at least one oxygen or a nitrogen or a phosphorus, (c) a chloroalkylaluminum compound, and (d) another organic compound that contains sulfur. The organic additives that are proposed in this composition make it possible to monitor the distribution of the oligomers that are produced by limiting those that are greater than C22.

The Japanese patent JP 58146518 claims a catalytic composition that makes it possible to dimerize ethylene into butene-1, comprising an alkoxy or alkyloxy phenoxy complex of titanium in the presence of triethylaluminum and a phosphine ($Ph_3P$).

The U.S. Pat. No. 3,584,071 claims a catalytic composition for the oligomerization of ethylene, comprising diphenyl ether that is combined with titanium tetrachloride and ethyl aluminum sesquichloride to increase the proportion of oligomers from C10 to C18.

In the patent EP 0,722,922 B1, the IPCL Company claims a catalytic composition that comprises a tetraphenoxy titanium compound $Ti(OAr)_4$, in which OAr is a phenoxy group that is ortho-substituted or para-substituted or both by alkyl chains, whereby the activator is an alkylaluminum and in particular ethyl aluminum sesquichloride, to oligomerize the ethylene into a mixture of C4 to C36 alpha-olefins. The addition of an organic compound that contains a heteroatom that is based on sulfur, oxygen or phosphorus makes it possible to improve the monitoring of the distribution of olefins.

Other compounds of titanium or zirconium that comprise two phenoxy entities that are linked to one another or a phenoxy ligand and a cyclopentadienyl ligand that may or may not be connected to one another, or else a phenoxy-imine- or phenoxy-amido-type chelating ligand are known for catalyzing the polymerization of ethylene in the presence of various activators including methylaluminoxane, whereby the polymerization of ethylene implements a number of patterns of greater than 100 in a manner known to one skilled in the art and makes it possible to obtain solid polymers.

The primary drawback of the catalytic systems that are based on titanium or zirconium that involve the phenoxy ligands and lead to the formation of oligomers from ethylene is the formation of polymers in addition to the oligomers, which can also be the cause of a quick deactivation of the catalyst. The monitoring of the distribution of these oligomers is a very significant parameter for the industrial future of this type of catalytic system. In the majority of the systems, this distribution monitoring is associated with the use of additives (organic, etc.), which very often complicates the catalytic composition.

One objective of the invention is to provide a process for oligomerization of the olefins that implements a simplified catalytic composition that does not contain external additives, organic additives, etc., and is therefore a simple process that is easy to use.

Another objective of the invention is, in a preferred embodiment, to provide a process for oligomerization of the olefins that use a catalytic composition that makes it possible to obtain a very high butene selectivity.

Another objective of the invention is, in a preferred embodiment, to provide a process for oligomerization of the olefins that uses a catalytic composition that makes possible a monitoring of the distribution of the oligomers that are obtained. The process for oligomerization of the olefins according to the invention makes it possible to obtain a shorter oligomer distribution, in a very preferred manner of C2 to C14. One advantage of the invention is therefore to provide a selective process for oligomerization of the olefins over a range of oligomers.

It has now been found that a process for oligomerization of the olefins into compounds or into a mixture of compounds of general formula CpH2p with 4≤p≤80 that implements a catalytic composition comprising at least one organometallic complex of an element of the group IV that is selected from among titanium, zirconium or hafnium, whereby said organometallic complex contains at least one aryloxy-type (or phenoxy-type) ligand that is functionalized by a heteroatom that is selected from among nitrogen, oxygen, phosphorus or sulfur or by an aromatic group, whereby said organometallic complex has the following for a general formula:

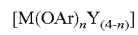

in which:
M is an element from the group IV that is selected from among titanium, zirconium, or hafnium,
Y is an atom of chlorine, bromine, a hydrocarbyl radical that comprises 1 to 30 carbon atoms, or a radical that is selected from the group that is formed by the alkoxy R'O—, the amido R'2N—, or the carboxylates R'COO—, where R' is a hydrocarbyl radical that comprises 1 to 30 carbon atoms,
n can assume the integer values of 1 to 4,
The ligand —OAr is an organic compound that is selected from the family of aryloxy (or phenoxy) ligands whose general structure is proposed below:

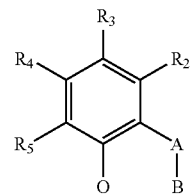

in which:
the groups R2, R3, R4 and R5, identical or different, consist of a hydrogen atom, a halogen or a hydrocarbyl radical that comprises 1 to 30 carbon atoms,
the functional group B is characterized by the presence of a heteroatom that is selected from among nitrogen, oxygen, phosphorus or sulfur, or by the presence of an aromatic group, whereby said functional group B can be directly linked to aryloxy or linked to another group that is directly linked to aryloxy and represented by the group A, also called a spacer group, whereby said spacer group A is a hydrocarbon chain that may or may not be cyclic, comprising 1 to 5 carbon atoms, made it possible to obtain a selectivity that is improved for the oligomerization of olefins and to limit the formation of polymers, preferably without an additional outside additive.

Thus, the catalytic composition that is used in the process for oligomerization of the olefins according to the invention is defined as comprising:

At least one organometallic complex of an element of group IV that is selected from among titanium, zirconium or hafnium that contains at least one aryloxy-type (or phenoxy-type) ligand that is functionalized by a heteroatom that is selected from among nitrogen, oxygen, phosphorus or sulfur or by an aromatic group, And optionally a hydrocarbylaluminum compound, called an activating agent, selected from the group that is formed by the tris(hydrocarbyl)aluminum compounds and the chlorinated or brominated hydrocarbylaluminum compounds, and the aluminoxanes.

According to a preferred embodiment, Y is preferably a radical that is selected from the group that is formed by the alkoxy R'O—.

According to a preferred embodiment, M is an element of the group IV that is selected from among titanium or zirconium.

According to a very preferred embodiment, M is titanium.

According to another very preferred embodiment, M is zirconium.

According to a preferred embodiment, said groups R2, R3, R4 and R5 are a methyl, ethyl, isopropyl, n-butyl, tert-butyl or cyclohexyl radical.

According to a preferred embodiment, said spacer group A is selected from among the following groups: —$CH_2$—, —$C(CH_3)_2$— and —$(CH_2)_2$—.

According to a preferred embodiment, said functional group B is selected from among the following groups: methoxy (—OMe), dimethylamino (—NMe2), pyrrolidino and phenyl.

According to a very preferred embodiment, said functional group B is selected from among the following groups: methoxy (—OMe), dimethylamino (—NMe2) and pyrrolidino.

Without being tied by any theory, the functional group B that is characterized by the presence of a heteroatom that is selected from among nitrogen, oxygen, phosphorus or sulfur or by the presence of an aromatic group is able to interact with the metal center M by forming a connection of, for example, the dative type that thus promotes the formation of the active complex in catalysis and contributes to its stability.

Several nonlimiting examples of phenoxy ligands that correspond to this definition are proposed below:

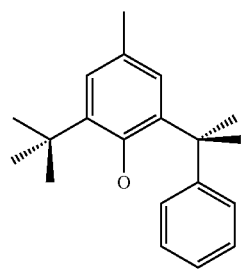

L1

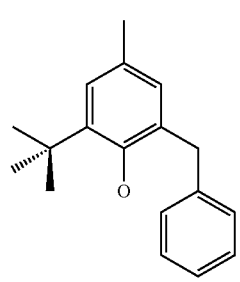

L2

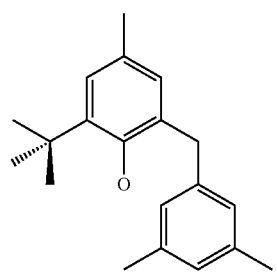

L3

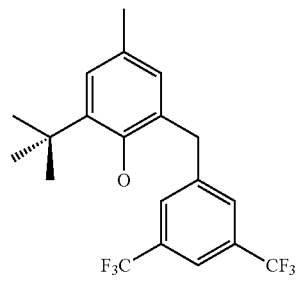

L4

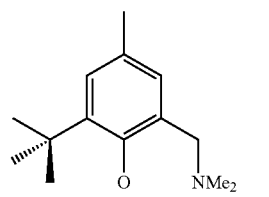

L5

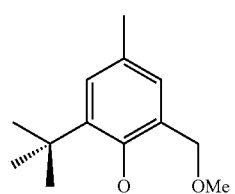

L6

L7
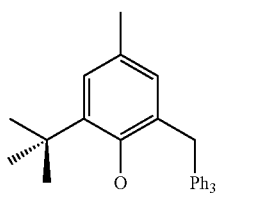
L8
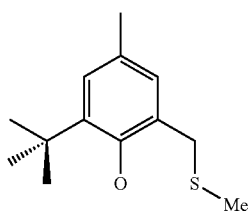
L9
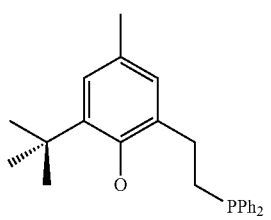
L10
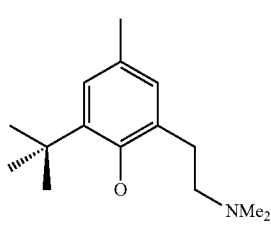
L11
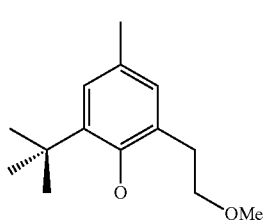
L12
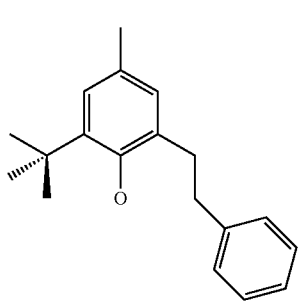
L13
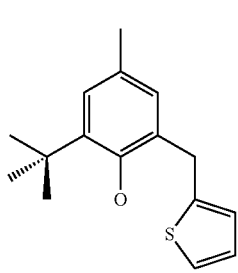
L14
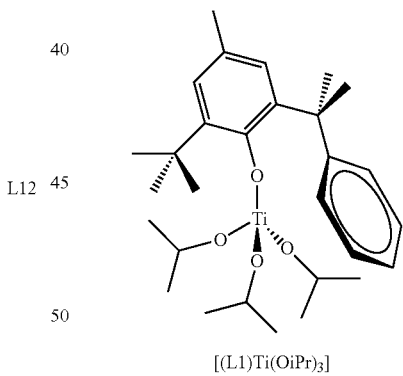
(first ligand image on right at top — pyrrolidine)
L15
L16
Several nonlimiting examples of organometallic complexes of the catalytic composition that is used in the process according to the invention are shown below:
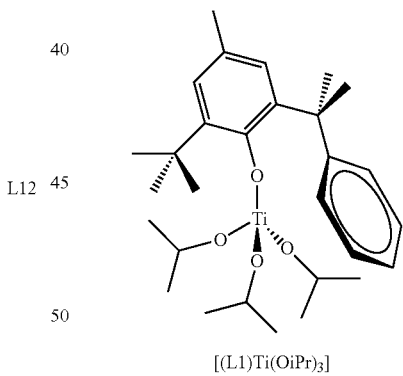
[(L1)Ti(OiPr)$_3$]
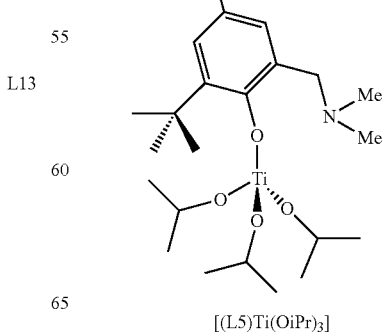
[(L5)Ti(OiPr)$_3$]

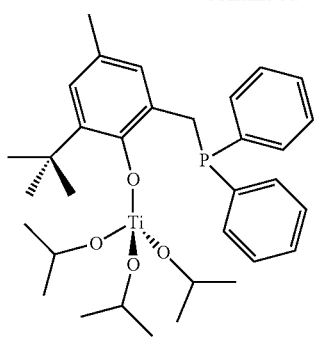
[(L7)Ti(OiPr)₃]
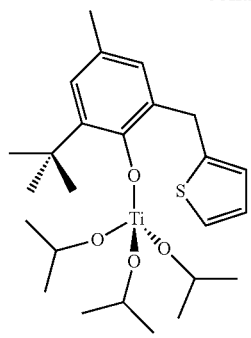
[(L13)Ti(OiPr)₃]
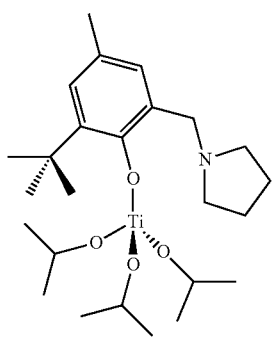
[(L14)Ti(OiPr)₃]
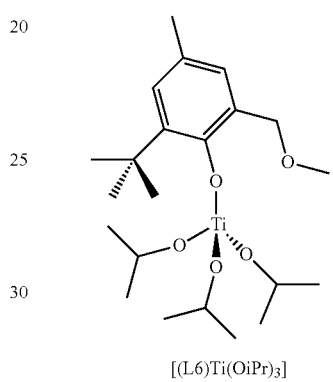
[(L6)Ti(OiPr)₃]
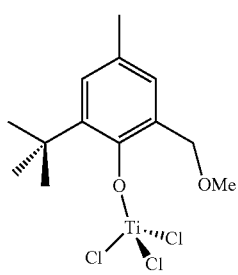
[(L6)TiCl₃]
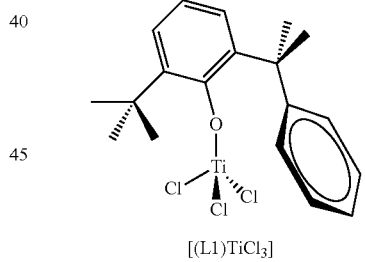
[(L1)TiCl₃]
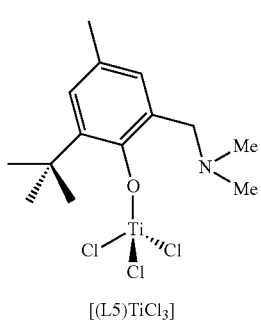
[(L5)TiCl₃]
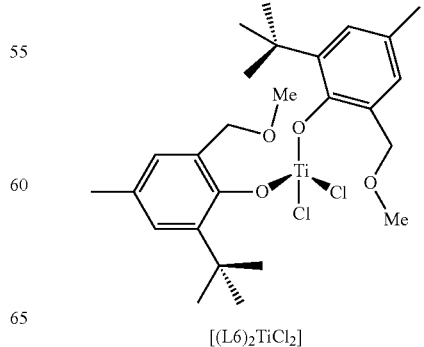
[(L6)₂TiCl₂]

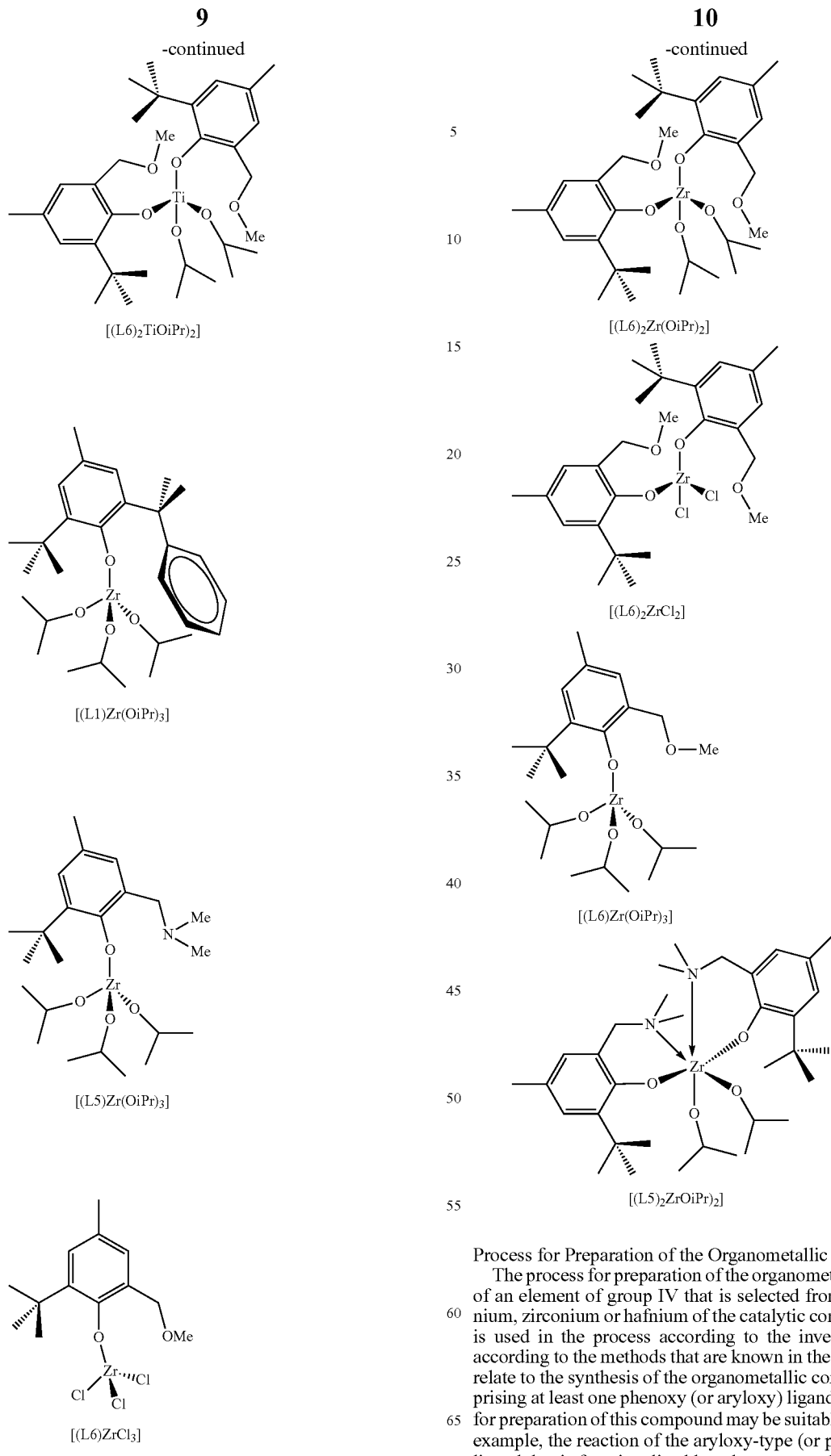

Process for Preparation of the Organometallic Complex

The process for preparation of the organometallic complex of an element of group IV that is selected from among titanium, zirconium or hafnium of the catalytic composition that is used in the process according to the invention is done according to the methods that are known in the literature that relate to the synthesis of the organometallic complexes comprising at least one phenoxy (or aryloxy) ligand. Any process for preparation of this compound may be suitable, such as, for example, the reaction of the aryloxy-type (or phenoxy-type) ligand that is functionalized by a heteroatom that is selected from among nitrogen, oxygen, phosphorus or sulfur or by an aromatic group, with a salt of an element of group IV that is selected from among titanium, zirconium or hafnium in an organic solvent, such as, for example, an ether, an alcohol, an alkane such as, for example, pentane, an aromatic solvent such as, for example, toluene, or a chlorinated solvent such as, for example, dichloromethane.

According to a preferred embodiment of said process for preparation, the organometallic complex is prepared in situ in the solvent that is used for the oligomerization reaction. In this case, the mixing order of the salt of the element of group IV is selected from among titanium, zirconium or hafnium, and the ligand is not critical. However, in a preferred manner, a solution of a compound of the element of group IV that is selected from among titanium, zirconium or hafnium that is soluble in an organic medium is first prepared, and then the aryloxy-type (or phenoxy-type) ligand that is functionalized by a heteroatom that is selected from among nitrogen, oxygen, phosphorus or sulfur or by an aromatic group is added.

According to another preferred embodiment of said process for preparation, said organometallic complex is isolated before solubilization in the solvent of the oligomerization reaction.

The catalytic composition that is used in the process according to the invention also advantageously comprises a hydrocarbylaluminum compound that is called an activating agent. The hydrocarbylaluminum compounds are advantageously selected from the group that is formed by tris(hydrocarbyl)aluminum, chlorinated or brominated hydrocarbylaluminum compounds, and aluminoxanes. The tris(hydrocarbyl)aluminum and the chlorinated or brominated hydrocarbylaluminum compounds preferably correspond to the general formula $AlR''_xZ_{3-x}$ in which R'' represents a monovalent hydrocarbon radical that contains, for example, up to 12 carbon atoms such as alkyl, aryl, aralkyl, alkyl or cycloalkyl, Z represents a halogen atom that is selected from among, for example, chlorine and bromine, whereby Z is preferably a chlorine atom, and x assumes a value of 1 to 3. As examples of such compounds of formula $AlR''_xZ_{3-x}$, it is possible to mention ethyl aluminum sesquichloride (EASC), dichloroethylaluminum, dichloroisobutyl-aluminum, chlorodiethylaluminum, methylaluminoxane (MAO), modified methylaluminoxane (MMAO), and triethylaluminum (TEA). These activating agents can be used by themselves or in a mixture.

According to the nature of the organometallic complex of an element of group IV that is selected from among titanium, zirconium or hafnium $[M(OAr)_nY_{(4-n)}]$, the activating agent can also be selected from the group of Lewis acids of the tris(aryl)-borane type, such as tris(perfluorophenyl)borane, tris(3,5-bis(trifluoromethyl)phenyl)-borane, tris-(2,3,4,6-tetrafluorophenyl)borane, tris(perfluoronaphthyl)borane, tris(perfluorobiphenyl)borane and derivatives thereof.

As an activator, it is also possible to use an (aryl)borate combined with a triphenylcarbenium cation or with a trisubstituted ammonium cation, such as triphenylcarbenium tetrakis(perfluorophenyl)borate, N,N-dimethylanilinium tetrakis(perfluorophenyl)borate, N,N-diethylanilinium tetrakis(3,5-bis(trifluoromethyl)phenyl)borate, or triphenylcarbenium tetrakis(3,5-bis(trifluoromethyl)phenyl) borate.

Process for Preparation of the Catalytic Composition that is Used in the Process According to the Invention.

According to a preferred embodiment of the process for preparation of said catalytic composition and when an activating agent is used, the two components of said catalytic composition, i.e., the organometallic complex and the activating agent, can be brought into contact in any order in a solvent that is selected from the group that is formed by aliphatic and cycloaliphatic hydrocarbons such as hexane, cyclohexane, heptane, butane or isobutane, by an unsaturated hydrocarbon such as a monoolefin or a diolefin that comprises, for example, 4 to 20 carbon atoms, by an aromatic hydrocarbon such as benzene, toluene, ortho-xylene, mesitylene, ethylbenzene or by a chlorinated hydrocarbon such as chlorobenzene or dichloromethane, pure or in a mixture. Advantageously, the aliphatic hydrocarbons such as n-heptane and the aromatic hydrocarbons such as ortho-xylene are used.

According to another preferred embodiment of the process for preparation of said catalytic composition and when an activating agent is used, the activating agent is added in a solution that contains the organometallic complex of the element of group IV that is selected from among titanium, zirconium, or hafnium.

The concentration of the element of group IV that is selected from among titanium, zirconium or hafnium in the catalytic solution is advantageously between $1.10^{-4}$ to 1 mol/l, preferably from $1.10^{-3}$ to 0.5 mol/l.

The molar ratio between the optional activating agent and the organometallic complex of the element of group IV that is selected from among titanium, zirconium or hafnium is advantageously between 1/1 and 1800/1, preferably from 2/1 to 800/1, and in a preferred manner between 2/1 and 500/1.

The temperature at which the components of the catalytic system are mixed is advantageously between −10 and +180° C., preferably between 0 and +150° C., for example at a temperature that is close to ambient temperature (15 to 30° C.). The mixing can be carried out under an atmosphere of ethylene or inert gas.

Oligomerization Reaction

The process according to the invention is a process for oligomerization of olefins for producing compounds or a mixture of compounds of general formula $C_pH_{2p}$ with $4 \leq p \leq 80$, preferably with $4 \leq p \leq 50$, in a preferred manner with $4 \leq p \leq 26$, and in a more preferred manner with $4 \leq p \leq 14$, implementing the catalytic composition that is described above.

The feedstock that is used in the process for oligomerization according to the invention consists of C2-C12 alpha-olefins, and preferably the feedstock is selected from among ethylene, propylene, or butene, and very preferably, the feedstock is ethylene.

According to a preferred embodiment, the process is a process for dimerization of ethylene, and even more preferably, a process for selective dimerization of ethylene into butene-1.

According to a preferred embodiment, titanium is used as a metal, triethylaluminum is used as an activating agent, and a molar ratio of activating agent to organometallic complex of between 1 and 5 is used for the dimerization of ethylene.

According to another preferred embodiment, zirconium is used as a metal, ethyl aluminum sesquichloride is used as an activating agent, and a molar ratio of activating agent to organometallic complex of between 6 and 30 is used for the oligomerization of ethylene.

The oligomerization reaction of the olefins is advantageously carried out under a total pressure of 0.5 to 15 MPa, preferably 1 to 10 MPa, and at a temperature of 20 to 180° C., preferably 40 to 140° C.

According to a preferred embodiment, the catalytic oligomerization reaction is implemented intermittently. A selected volume of the catalytic solution that is constituted as described above is introduced into a reactor that is equipped with the usual stirring devices, heating devices and cooling devices, and then it is pressurized by ethylene to the desired pressure, and the temperature is adjusted to the desired value. The oligomerization reactor is kept at constant pressure by introducing ethylene until the total volume of liquid that is produced represents, for example, 2 to 50 times the volume of the catalytic solution originally introduced. The catalyst is then destroyed by any conventional means known to one skilled in the art, and then it is drawn off, and the products of the reaction and the solvent are separated.

According to another preferred embodiment, the catalytic oligomerization reaction is implemented continuously. The catalytic solution is injected at the same time as ethylene into a reactor that is stirred by standard mechanical means that are known to one skilled in the art or by an outside recirculation, and it is kept at the desired temperature. It is also possible to inject the components of the catalyst separately into the reaction medium. Ethylene is introduced by an intake valve that is controlled at the pressure that keeps the former constant. The reaction mixture is drawn off by means of a valve that is controlled at the liquid level so as to keep the former constant. The catalyst is continuously destroyed by any conventional means that is known to one skilled in the art, and then the products that are obtained from the reaction as well as the solvent are separated, for example by distillation. The ethylene that has not been transformed can be recycled in the reactor. The catalyst residues that are included in a heavy fraction can be incinerated.

Products that are Obtained:

The process according to the invention makes possible the production of compounds or a mixture of oligomer compounds of general formula $C_pH_{2p}$ with $4 \leq p \leq 80$, preferably with $4 \leq p \leq 50$, in a preferred manner with $4 \leq p \leq 26$, and in a very preferred manner with $4 \leq p \leq 14$. The compounds or mixture of oligomer compounds that are thus obtained are generally liquid oligomer compounds.

These compounds or mixture of compounds find a use, for the lower oligomers (C4, C6, C8, C10), as comonomers with ethylene in the manufacturing of linear low-density polyethylene or as a starting product for the manufacturing of lubricating synthesis oils, and for the olefins that have a chain length of C10 to C26 in the manufacturing of plasticizers and detergents.

The following examples illustrate the invention without limiting its scope.

EXAMPLE 1

Synthesis of the Complex [(L1)Ti(OiPr)$_3$]: Complex 1

3.43 g (9.51 mmol) of the lithium salt derivative of ligand L1 that is dissolved in 25 ml of THF is introduced into a 100 ml flask that is equipped with an argon intake and a magnetized bar. Then, a solution that contains 2.4 g (9.2 mmol) of [ClTi(OiPr)$_3$] in 15 ml of THF is added drop by drop. This reaction mixture is stirred continuously for 1 night at ambient temperature. The solvent is then evaporated under vacuum, and the residue is taken up with 30 ml of n-pentane. Several attempts to recrystallize the residue in n-pentane under cold conditions ultimately make it possible to isolate the complex 1 in the form of white crystals (m=3.63 g; Rdt=86.8%). The 1H and 13C NMR characterizations as well as the elementary analysis confirm the structure of the compound.

EXAMPLE 2

Synthesis of the Complex [(L5)Ti(OiPr)$_3$]: Complex 2

0.71 g (2.5 mmol) of [Ti(OiPr)$_4$] as well as 5 ml of diethyl ether are introduced into a 20 ml Schlenk flask. This solution is cooled to −30° C. before adding to it a solution that contains 0.55 g (2.5 mmol) of L5 in 10 ml of Et$_2$O. A color change to yellow is observed. The temperature is then allowed to rise to ambient temperature, and the mixture is stirred for one night. The volatile compounds are then eliminated under vacuum, and 1.02 g of complex 2 is recovered in the form of a yellow oil (Rdt=92%). The 1H and 13C NMR characterizations as well as the elementary analysis confirm the structure of the compound.

EXAMPLE 3

Synthesis of the Complex [(L6)$_2$Ti(OiPr)$_2$]: Complex 3

1.42 g (1.5 ml, 5 mmol) of [Ti(O$^i$Pr)$_4$] as well as 10 ml of diethyl ether are introduced into a 20 ml Schlenk flask. This solution is cooled to −30° C. before adding thereto a solution that contains 1.04 g (5 mmol) of ligand L6 in 20 ml of Et$_2$O. A color change to yellow is then observed. After a return to ambient temperature, the reaction mixture is stirred for one additional night. The volatile compounds are then eliminated under vacuum until a yellow solid is obtained whose $^1$H NMR analysis reveals the presence of the mono-aryloxy/bis-aryloxy mixture. A selective crystallization of the complex 3 in a minimum amount of pentane at −18° C. leads to obtaining 678 mg of yellow crystals (Rdt=23.3%). The 1H and 13C NMR characterizations as well as the elementary analysis confirm the structure of the compound.

EXAMPLE 4

Synthesis of the Complex [(L5)$_2$Zr(OiPr)$_2$]: Complex 4

0.688 g (2.1 mmol) of [Zr(O$^i$Pr)$_4$] as well as 10 ml of toluene are introduced into a 20 ml Schlenk flask. A solution that contains 0.928 g (4.1 mmol) of L5 in 15 ml of toluene is slipped into this mixture. The mixture is stirred at 60° C. for 4 hours. The volatile compounds are then eliminated under vacuum, and 1.39 g of complex 4 is recovered in the form of a white solid (quantitative yield). The 1H and 13C NMR characterizations as well as the elementary analysis confirm the structure of the compound.

EXAMPLE 5

Synthesis of the Complex [(L6)$_2$Zr(OiPr)$_2$]: Complex 5

0.408 g (1.25 mmol) of [Zr(O$^i$Pr)$_4$] as well as 10 ml of dichloromethane are introduced into a 20 ml Schlenk flask. This mixture is stirred at ambient temperature before adding thereto a solution that contains 0.520 g (2.5 mmol) of L6 in 10 ml of dichloromethane. The mixture is stirred for one night. The volatile compounds are then eliminated under vacuum. The viscous solid that is obtained is taken up in 5 ml of pentane, making it possible to isolate 0.555 g of a white solid (yield=71.1%). The 1H and 13C NMR characterizations as well as the elementary analysis confirm the structure of the compound.

EXAMPLE 6

Synthesis of the Complex [(L6)Zr(OiPr)$_3$]: Complex 6

0.408 g (1.25 mmol) of [Zr(OiPr)$_4$] as well as 5 ml of dichloromethane are introduced into a 20 ml Schlenk flask.

This mixture is stirred at ambient temperature before adding thereto a solution that contains 0.260 g (1.25 mmol) of L6 in 15 ml of dichloromethane. The mixture is stirred for 2 hours at 20° C. The volatile compounds are then eliminated under vacuum. The viscous solid that is obtained is taken up in 5 ml of pentane, concentrated under vacuum, and stored at 4° C. for 12 hours, making it possible to isolate 0.52 g of a whitish solid (yield=87%). The 1H and 13C NMR characterizations as well as the elementary analysis confirm the structure of the compound.

EXAMPLE 7

Selective Dimerization of $C_2H_4$ by the Complex 1 [(L1)Ti(OiPr)$_3$]+TEA 0.46 mmol of triethylaluminum in solution in 3.2 ml of n-heptane is introduced in order under argon atmosphere, at 60° C., into a stainless steel autoclave with a useful volume of 100 ml, equipped with a double jacket that makes it possible to regulate the temperature by circulation of water or oil. Next, 0.15 mmol of the complex 1 [(L1)Ti(OiPr)$_3$], previously solubilized in 2 ml of n-heptane, or a molar ratio of Al/Ti=3.1 is introduced. Ethylene is then introduced into the autoclave so as to keep a constant pressure of 2 MPa. After 1 hour of reaction, the introduction of ethylene is stopped. 1 ml of water is then injected under pressure into the autoclave by means of an airlock that it is possible to bring to a higher pressure than that of the autoclave. The autoclave is then depressurized, and a gas fraction and a liquid fraction that are analyzed by chromatography are collected. A small quantity of polyethylene is also recovered.

The material balance of the reaction shows that 1.9 g of oligomers has formed, which corresponds to a specific activity or hourly productivity of the catalyst that corresponds to the oligomer mass that is formed per gram of metal and per hour, equal to 267 g of oligomers/g of titanium/hour. The composition of the oligomers is as follows:

Butenes: 81.5% by weight % of butene-1 in the butenes: 99.3%
Hexenes: 16.2% by weight % of hexene-1 in the hexenes: 3.3%
Octenes: 0.8% by weight % of octene-1 in the octenes: 0%
Decenes: 0% % of decene-1 in the decenes: 0%
PE: 1.4%

EXAMPLE 8

Selective Dimerization of $C_2H_4$ by the Complex 2 [(L5)Ti(OiPr)$_3$]+TEA

The method that is described in Example 10 has been used: The 100 ml reactor is charged with 0.45 mmol of triethylaluminum in solution in 3.2 ml of n-heptane. 0.15 mmol of the complex 2 [(L5)Ti(OiPr)$_3$], previously solubilized in 2 ml of n-heptane (or a molar ratio of Al/Ti=3), is then introduced. The temperature is kept at 60° C. while introducing ethylene into the autoclave so as to keep a constant pressure of 2 MPa. After 1 hour of reaction, the introduction of ethylene is stopped. The material balance of the reaction shows that 12.6 g of oligomers has formed, which corresponds to a specific activity or hourly productivity that is equal to 2095 g of oligomers/g of titanium/hour. The composition of the oligomers is as follows:

Butenes: 91.6% by weight % of butene-1 in the butenes: 99.5%
Hexenes: 6.9% % of hexene-1 in the hexenes: 10.5%
Octenes: 0.1% % of octene-1 in the octenes: 0%
Decenes: 0.1% % of decene-1 in the decenes: 0%
PE 1.3%

EXAMPLE 9

Selective Dimerization of $C_2H_4$ by the Complex 3 [(L6)$_2$Ti(OiPr)$_2$]+TEA

The method that is described in Example 10 has been used: the 100 ml reactor is charged with 0.46 mmol of triethylaluminum in solution in 3.2 ml of n-heptane. 0.15 mmol of the complex 3 [(L6)$_2$Ti(OiPr)$_2$], previously solubilized in 2 ml of n-heptene (or a molar ratio of Al/Ti=3.1), is then introduced. The temperature is then kept at 60° C. while introducing ethylene into the autoclave so as to keep a constant pressure of 2 MPa. After 1 hour of reaction, the introduction of ethylene is stopped. The material balance of the reaction shows that 13.34 g of oligomers has formed, which corresponds to a specific activity or hourly productivity that is equal to 1806 g of oligomers/g of titanium/hour. The composition of the oligomers is as follows:

Butenes: 90.4% by weight % of butene-1 in the butenes: 99.3%
Hexenes: 8.0% % of hexene-1 in the hexenes: 1.2%
Octenes: 0.6% % of octene-1 in the octenes: 0%
Decenes: 0.3% % of decene-1 in the decenes: 0%
PE: 0.7%

EXAMPLE 10

Oligomerization of $C_2H_4$ by the Complex 4 [(L5)$_2$Zr(OiPr)$_2$]+EASC

The 100 ml reactor is charged with 28 ml of dry o-xylene and then brought to 80° C. 1.65 mmol of ethyl aluminum sesquichloride in solution in 1.7 ml of o-xylene is introduced into the autoclave. Next, 0.15 mmol of the complex 4 [(L5)$_2$Zr(OiPr)$_2$], previously solubilized in 2 ml of o-xylene (or a molar ratio of Al/Zr=22), is introduced. Next, the ethylene is injected into the reactor so as to keep a constant pressure of 5 MPa. After 1 hour of reaction, the introduction of ethylene is stopped, and 4.8 mmol of dodecylamine in solution in 2 ml of o-xylene is introduced into the autoclave to neutralize the catalyst. The material balance of the reaction shows that 16.7 g of oligomers has formed, which corresponds to a specific activity or hourly productivity that is equal to 1267 g of oligomers/g of zirconium/hour. The composition of the oligomers is as follows:

Butenes: 57.9% by weight % of butene-1 in the butenes: 99.2%
Hexenes: 25.8% % of hexene-1 in the hexenes: 99%
Octenes: 10.2% % of octene-1 in the octenes: 93.3%
Decenes: 4.1% % of decene-1 in the decenes: 80.6%
Dodecenes: 1.1% % of dodecene-1 in the dodecenes: 86.0%

EXAMPLE 11

Oligomerization of $C_2H_4$ by the Complex 5 [(L6)$_2$Zr(OiPr)$_2$]+EASC

The method that is described in Example 14 was used: the 100 ml reactor charged with 28 ml of o-xylene is brought to 80° C. before the introduction of 1.65 mmol of ethyl aluminum sesquichloride in solution in 1.7 ml of o-xylene. Next, 0.15 mmol of the complex 5 [(L6)$_2$Zr(OiPr)$_2$], previously solubilized in 2 ml of o-xylene, or a molar ratio of Al/Zr=22, is introduced. Next, ethylene is injected into the reactor so as to keep a constant pressure of 5 MPa. After 1 hour of reaction, the introduction of ethylene is stopped, and 4.8 mmol of dodecylamine in solution in 2 ml of o-xylene is introduced into the autoclave to neutralize the catalyst. The material balance of the reaction shows that 11.87 g of oligomers has formed, which corresponds to a specific activity that is equal to 409 g of oligomers/g of zirconium/hour. The composition of the oligomers is as follows:

Butenes: 59.9% by weight % of butene-1 in the butenes: 98.5%
Hexenes: 24.6% % of hexene-1 in the hexenes: 95.5%
Octenes: 9.4% % of octene-1 in the octenes: 89.9%
Decenes: 4.4% % of decene-1 in the decenes: 75%
Dodecenes: 1.4%
Tetradecenes: 0.3%

EXAMPLE 12

Oligomerization of $C_2H_4$ by the Complex 6 [(L6)Zr(OiPr)$_3$]+EASC

The method that is described in Example 14 was used: the 100 ml reactor charged with 28 ml of o-xylene is brought to 80° C. before introducing 1.65 mmol of ethyl aluminum sesquichloride in solution in 1.7 ml of o-xylene. Next, 0.15 mmol of the complex 6, previously solubilized in 2 ml of o-xylene (or a molar ratio of Al/Zr=22), is introduced. Next, ethylene is injected into the reactor so as to keep a constant pressure of 5 MPa. After 1 hour and 40 minutes of reaction, the introduction of ethylene is stopped, and 4.8 mmol of dodecylamine in solution in 2 ml of o-xylene is introduced into the autoclave to neutralize the catalyst. The material balance of the reaction shows that 25.55 g of oligomers has formed, which corresponds to a specific activity or hourly productivity that is equal to 1112 g of oligomers/g of zirconium/hour. The composition of the oligomers is as follows:

Butenes: 60.4% by weight % of butene-1 in the butenes: 99.8%
Hexenes: 24.9% % of hexene-1 in the hexenes: 96.6%
Octenes: 9.4% % of octene-1 in the octenes: 93.5%
Decenes: 3.7% % of decene-1 in the decenes: 81.9%
Dodecenes: 1.1%
Tetradecenes: 0.5%
PE: 0.04%

The invention claimed is:
1. A process comprising catalytically oligomerizing olefins into compounds or into a mixture of compounds of formula $C_pH_{2p}$ with 4≤p≤80, the catalyst being a catalytic composition comprising at least one organometallic complex of an element of group IV, which is titanium, zirconium or hafnium, wherein said organometallic complex contains at least one aryloxy ligand functionalized by a heteroatom, which is nitrogen, oxygen, phosphorus or sulfur or by an aromatic group, said organometallic complex having the following formula:

[M(OAr)$_n$Y$_{(4-n)}$]

wherein:
M is an element from group IV, which is titanium, zirconium, or hafnium,
Y is an atom of chlorine, or bromine, or a hydrocarbyl radical that comprises 1 to 30 carbon atoms, or a radical, which is alkoxy R'O—, amido R'$_2$N—, or carboxylate R'COO—, where R' is a hydrocarbyl radical comprising 1 to 30 carbon atoms,
n is an integer of 1 to 4,
the ligand —OAr is an aryloxy ligand of the formula:

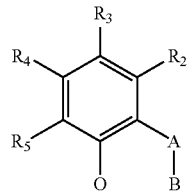

in which:
R$_2$, R$_3$, R$_4$ and R$_5$, identical or different, represent a hydrogen atom, a halogen, or a hydrocarbyl radical that comprises 1 to 30 carbon atoms,
B is methoxy (—OMe), dimethylamino (—NMe$_2$), or pyrrolidino, and A is —CH$_2$—, —C(CH$_3$)$_2$— or —(CH$_2$)$_2$—.

2. The process for oligomerization of olefins according to claim 1, in which said catalytic composition further comprises a hydrocarbylaluminum activating agent, which is a tris(hydrocarbyl)aluminum compound or a chlorinated or brominated hydrocarbylaluminum compound or an aluminoxane.

3. The process for oligomerization of olefins according to claim 1, in which said catalytic composition does not comprise external additives.

4. The process for oligomerization of olefins according to claim 1, in which said spacer group A is —C(CH$_3$)$_2$— or —(CH$_2$)$_2$—.

5. The process for oligomerization of olefins according to claim 4, in which B is or pyrrolidino.

6. The process for oligomerization of olefins according to claim 4, in which B is methoxy (—OMe).

7. The process for oligomerization of olefins according to claim 1, in which M is titanium.

8. The process for oligomerization of olefins according to claim 1, in which M is zirconium.

9. The process for oligomerization of olefins according to claim 2, wherein the olefins comprise at least one of ethylene, propylene, or butene.

10. The process for oligomerization of olefins according to claim 9, in which the olefins comprise ethylene.

11. The process for oligomerization of olefins according to claim 10, in which the process is dimerization of ethylene.

12. The process for oligomerization of olefins according to claim 11, which is selective dimerization of ethylene into 1-butene.

13. The process for oligomerization of olefins according to claim 1, which is carried out under a total pressure of 0.5 to 15 MPa, and at a temperature of 20 to 180° C.

14. The process for oligomerization of olefins according to claim 1, which is implemented intermittently.

15. The process for oligomerization of olefins according to claim 1, which is implemented continuously.

16. The process for oligomerization of olefins according to claim 2, wherein said catalyst composition has a molar ratio between the activating agent and said organometallic complex of the element of group IV that is titanium, zirconium, or hafnium of between 1/1 and 1800/1.

17. The process for oligomerization of olefins according to claim 11, in which M is titanium, the activating agent is triethylaluminum, with a molar ratio of activating agent to organometallic complex of between 1/1 and 5/1.

18. The process for oligomerization of olefins according to claim 2, in which M is zirconium, ethyl aluminum sesquichloride is the activating agent, with a molar ratio of activating agent to organometallic complex of between 6/1 and 30/1.

19. The process for oligomerization of olefins according to claim 1, in which p is between 4 and 50.

20. The process for oligomerization of olefins according to claim 19, in which p is between 4 and 26.

21. The process for oligomerization of olefins according to claim 19, in which p is between 4 and 14.

22. A process comprising catalytically oligomerizing olefins into compounds or into a mixture of compounds of formula $C_pH_{2p}$ with $4 \leq p \leq 80$, the catalyst being a catalytic composition comprising at least one organometallic complex of an element of group IV, which is titanium, zirconium or hafnium, wherein said organometallic complex contains at least one aryloxy ligand functionalized by a heteroatom, which is nitrogen, oxygen, phosphorus or sulfur or by an aromatic group, said organometallic complex having the following formula:

[M(OAr)$_n$Y$_{(4-n)}$]

wherein:
M is an element from group IV, which is titanium, zirconium, or hafnium,
Y is an atom of chlorine, or bromine, or a hydrocarbyl radical that comprises 1 to 30 carbon atoms, or a radical, which is alkoxy R'O—, amido R'$_2$N—, or carboxylate R'COO—, where R' is a hydrocarbyl radical comprising 1 to 30 carbon atoms,
n is an integer of 1 to 4,
the ligand —OAr is an aryloxy ligand of one of the following groups

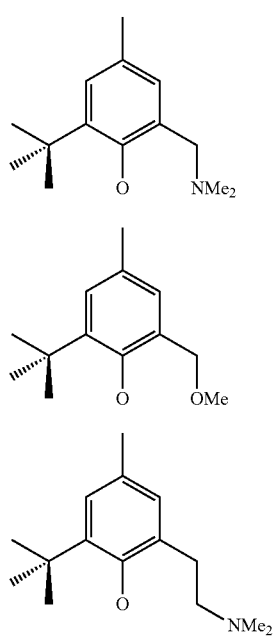

L5

L6

L10

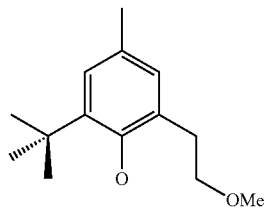

L11

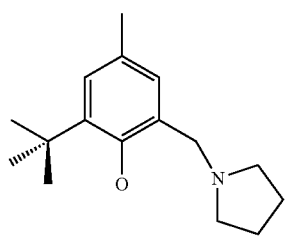

L14

23. A process comprising catalytically oligomerizing olefins into compounds or into a mixture of compounds of formula $C_pH_{2p}$ with $4 \leq p \leq 80$, the catalyst being a catalytic composition comprising at least one organometallic complex of an element of group IV, which is titanium, zirconium or hafnium, wherein said organometallic complex contains at least one aryloxy ligand functionalized by a heteroatom, which is nitrogen, oxygen, phosphorus or sulfur or by an aromatic group, said organometallic complex being one of the following compounds:

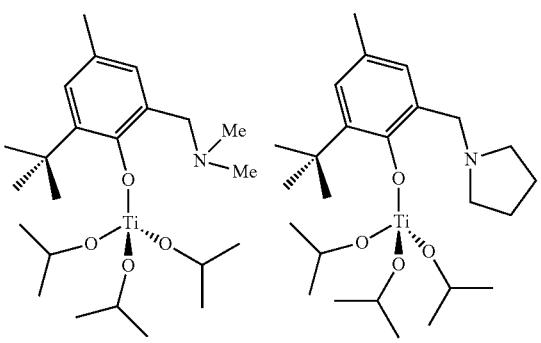

[(L5)Ti(OiPr)$_3$]   [(L14)Ti(OiPr)$_3$]

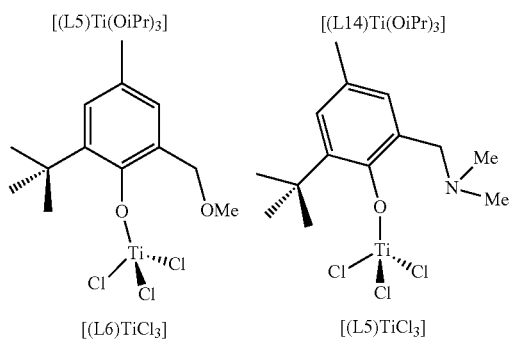

[(L6)TiCl$_3$]   [(L5)TiCl$_3$]

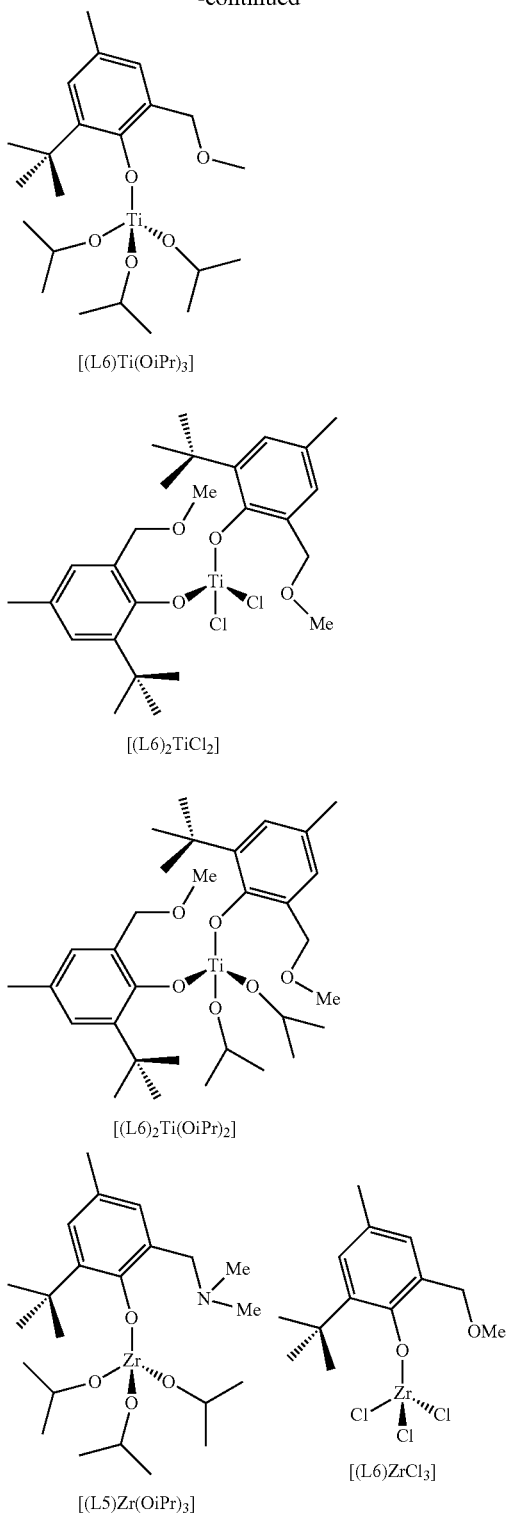
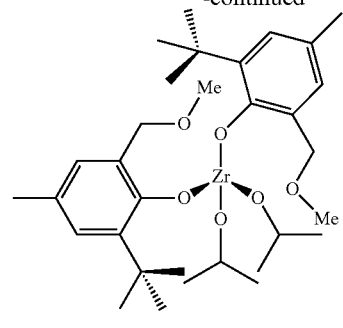
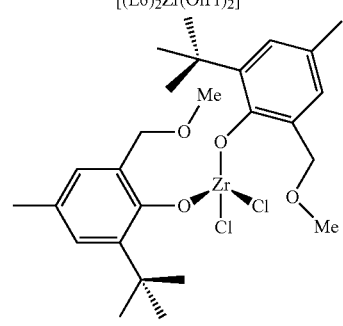
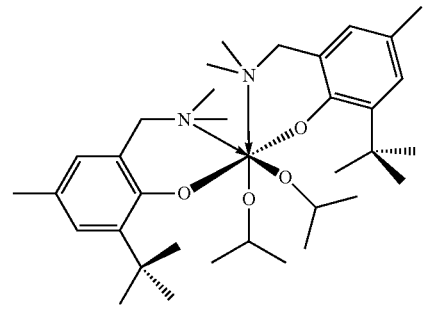
24. The process for oligomerization of olefins according to claim 4, in which B is dimethylamino (—NMe$_2$).
* * * * *